United States Patent [19]

Jacklich

[11] 4,444,560

[45] Apr. 24, 1984

[54] DENTAL INSTRUMENT-PDL SYRINGE

[76] Inventor: John Jacklich, 102 Western Court, Santa Cruz, Calif. 95060

[21] Appl. No.: 495,732

[22] Filed: May 20, 1983

Related U.S. Application Data

[63] Continuation of Ser. No. 320,551, Nov. 12, 1981, abandoned.

[51] Int. Cl.³ .............................................. A61M 1/00
[52] U.S. Cl. .................................... 604/224; 222/391
[58] Field of Search .............. 604/209, 208, 207, 186, 604/224; 433/89, 90, 80, 83; 222/391, 340

[56] References Cited

U.S. PATENT DOCUMENTS

| | | | |
|---|---|---|---|
| 844,544 | 2/1907 | Schimmel | 128/218 N |
| 977,282 | 11/1910 | De Vilbiss | 222/391 |
| 1,435,908 | 11/1922 | Muehl | 222/391 |
| 1,569,961 | 1/1926 | Bauchert | 128/218 N |
| 2,221,739 | 11/1940 | Reiter | 128/218 F |
| 2,472,116 | 6/1949 | Maynes | 128/218 F |
| 2,591,457 | 4/1952 | Maynes | 128/218 F |

FOREIGN PATENT DOCUMENTS 212625 12/1960 Austria ................................ 604/209

Primary Examiner—John D. Yasko
Attorney, Agent, or Firm—Robert G. Slick

[57] ABSTRACT

A compact anesthetic syringe is provided for injecting a medication under high pressure into a confined space. The instrument is particularly adapted for injecting a medication into the dental periodontal ligament (PDL) and may be used by any dentist without special training.

20 Claims, 7 Drawing Figures

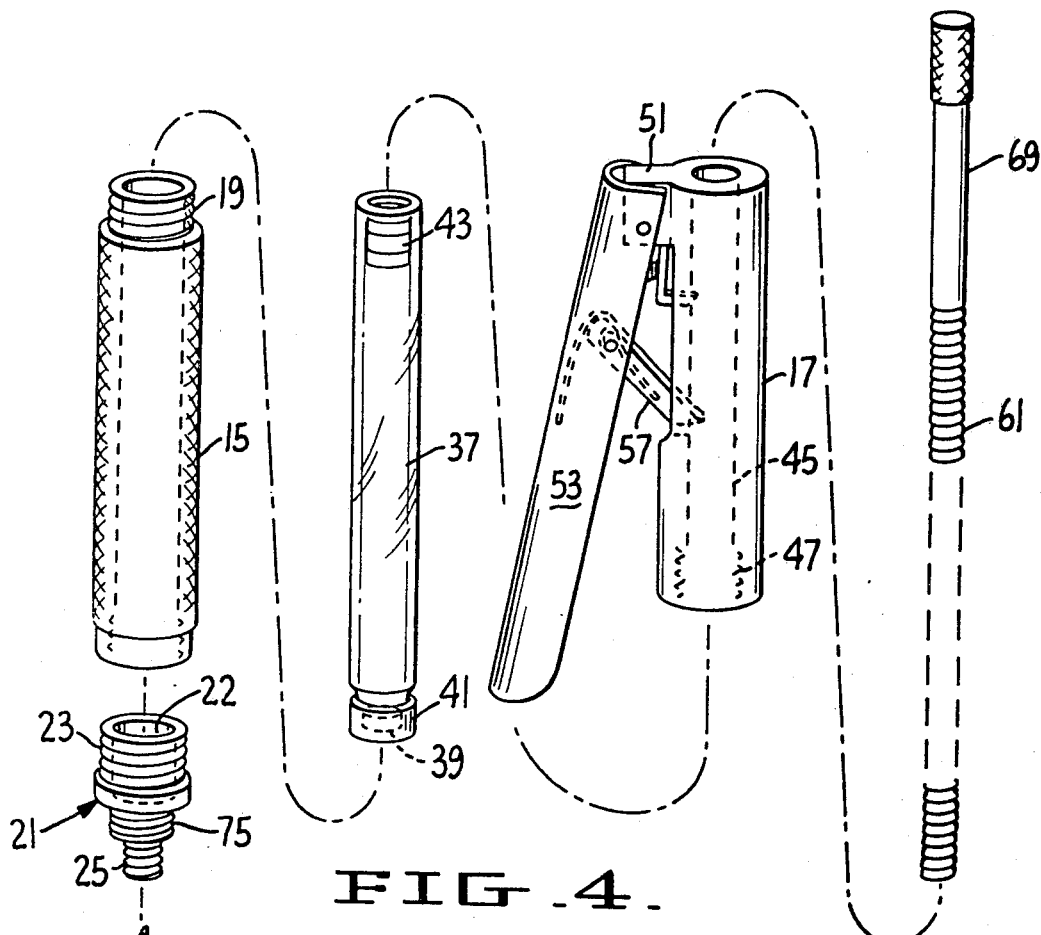
FIG_4.
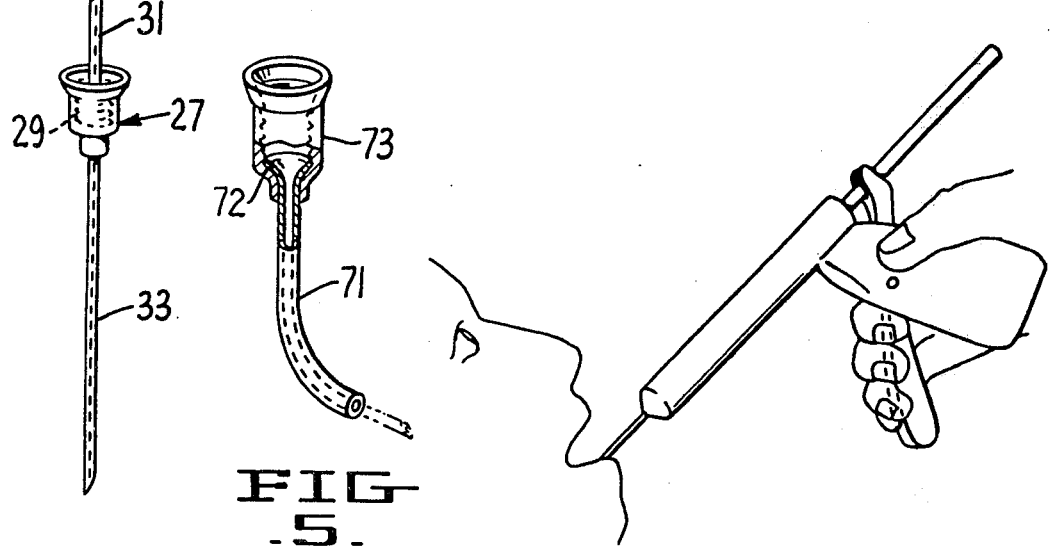
FIG_5.
FIG_6.
PRIOR ART

DENTAL INSTRUMENT-PDL SYRINGE

This application is a continuation of application Ser. No. 320,551, filed Nov. 12, 1981, now abandoned.

SUMMARY OF THE INVENTION

It is frequently necessary to inject a medication at a relatively high pressure into the human body and particularly into the dental periodontal ligament. A very fine needle must be used and that high pressure is required to force the medication into the tissues.

In the past rather cumbersome devices have been employed which were awkward for the dentist to use, which required a great deal of manual dexterity and, because of the rather large size and formidable appearance of the instruments, had a tendency to scare the patients.

In accordance with the present invention, a very compact device is employed which can be almost concealed in the hand.

Another feature of the present invention is that only a relatively slight movement is necessary to actuate the syringe so that the device is capable of exerting a high pressure with little movement by the operator so that the operator can concentrate on getting the medication into the proper place rather than the operation of the syringe. Further, the device of the present invention may be calibrated, so that each movement of the injection lever will discharge a known amount of liquid.

Another object of the invention is to provide a device which fits within the hand of the dentist so that it is comfortable and natural to "aim" the device at a precise location. One may hold the device as one holds a pencil or it may be held between the thumb and palm, both of which are comfortable operating positions.

Other features and advantages of the invention will be brought out in the balance of the specification.

BRIEF DESCRIPTION OF THE DRAWINGS

FIG. 4 is an exploded view of the instrument.

FIG. 5 shows how the device may be used with an angle discharge device.

FIG. 6 is a perspective view of a prior art device.

DESCRIPTION OF THE PREFERRED EMBODIMENTS

Figures 1, 2, 2A, 3:
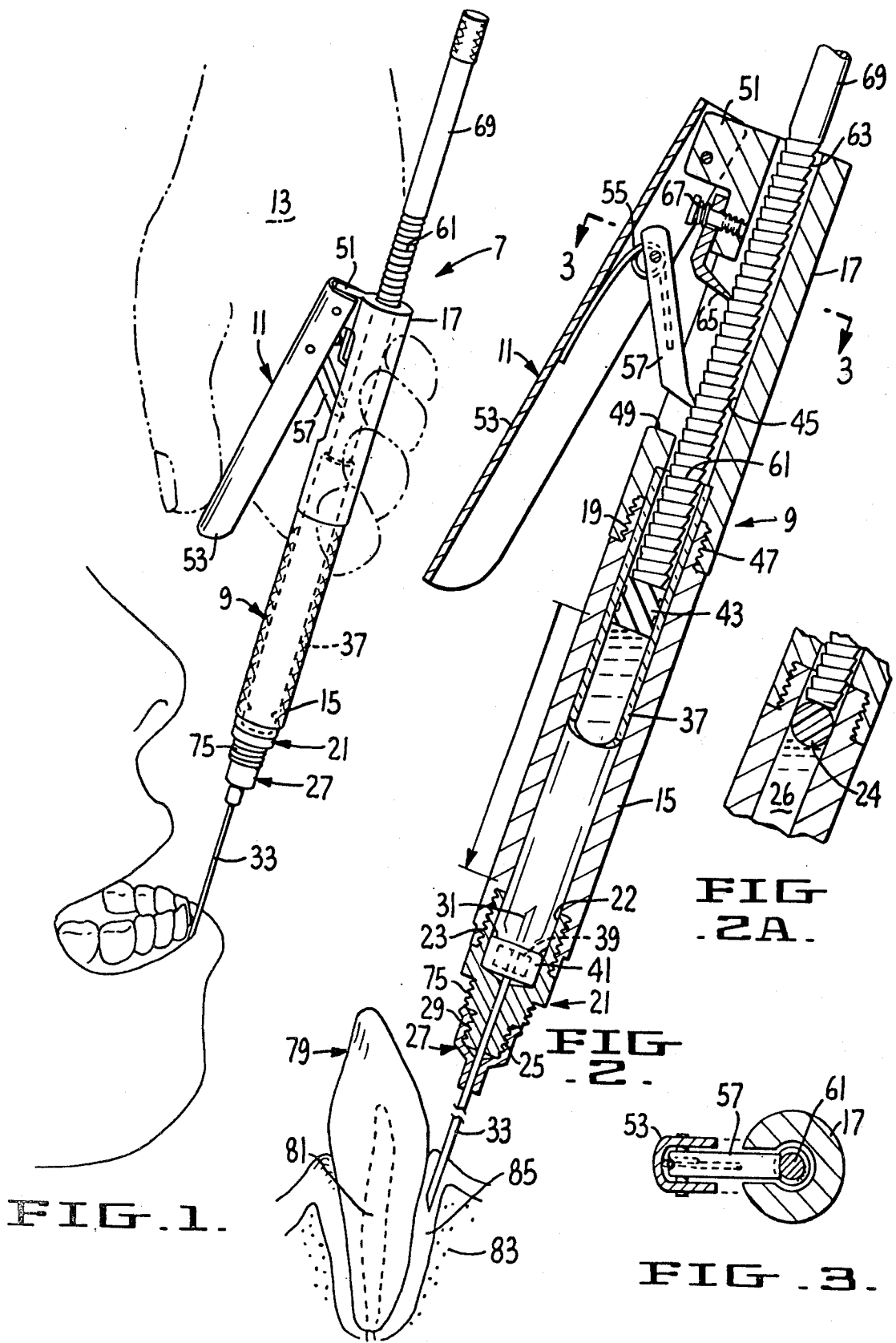
FIG. 1 is a perspective view showing an instrument embodying the present invention in use.
FIG. 2 is an enlarged view of the instrument, partly in section, showing it in use.
FIG. 2A shows how the device can be used with a bulk medication.
FIG. 3 is a section on the line 3—3 showing the different parts of the instrument.

Referring now to the drawings by reference characters, the device of the present invention is generally designated 7 and, as can be seen best in FIGS. 1 and 2 consists of a central tubular portion 9 and an operating handle 11. In FIG. 1 the device is shown being held in the palm of a hand 13 with the operating lever 11 being operated by the thumb.

The tubular portion 9 consists of a lower cylinder 15 and an upper cylinder 17 connected together by means of the threads 19.

At the distal end of the cylinder 15 is a nosepiece 21 which has external threads 23 for attaching it to the lower cylinder 15 and a second set of threads 25 which may be used for attaching it to the cannula assembly 27. The nosepiece 21 has a smooth, cylindrical inner surface 22 which serves to hold the end of a carpule 35, later described. The cannula assembly 27 includes a hub 29 with internal threads to mate with the threads 25. This holds the double ended cannula proper which has short end 31 which is adapted to extend into the nosepiece 21 and a longer external end 33 which is used for the actual injection of the medicine.

The device of the present invention is primarily adapted for use with a carpule 35 which consists of a glass cylinder 37, a fixed end portion 39, which is adapted to be penetrated by the short end 31 of the cannula and a metal shoulder 41. At the opposite end is a resilient piston-like member 43 which can be pushed into the cylinder 37 to discharge a medication contained therein.

The upper portion 17 of the cylinder 9 is generally round on the outside with a central passage 45 and with internal threads 47 near the bottom to mate with threads 19. Part 17 has a slot 49 at one side thereof and also has a lug 51 which extends outwardly just above the slot and the operating handle 53 is pivoted on this lug. A spring 55 normally biases the handle 53 outwardly. A ratchet 57 is pivoted on handle 53 and the same spring 55 biases ratchet 57 into the groove 49 as is best seen in FIG. 2.

A piston rod 61 extends into the opening 45 and the piston rod has a number of ratchet teeth 63. Preferably these teeth form a thread so that one can remove rod 61 by turning it. It will be noted that the ratchet teeth are substantially flat on one side and set at an angle on the opposite side so that the ratchet 57 can actuate the rod effectively. A pawl 65 is urged by spring 67 into contact with the ratchet teeth. Now it is obvious that as the handle 53 is worked back and forth, the piston rod 61 will advance into the cylinder and pawl 65 will prevent return motion. It will press downwardly upon the plug portion 43 of the carpule forcing the contents of the carpule out through cannula 33. By properly selecting the size of the ratchet teeth and the movement of the operating arm 53, each movement of the arm 53 will inject a known and measured quantity of the liquid from the carpule.

Although the device of the present invention is designed primarily to be used with a carpule, it may be also used with a bulk medication, as is shown in FIG. 2A, in which case it would only be necessary for the cannula to extend out from the nosepiece 21 and one would insert a small, inert, compressible ball 24 above the bulk liquid 26 to be dispensed, the ball serving as a piston to seal and discharge the contents.

It will be noted that the portion of the piston rod 61 near the proximal end is unthreaded as at 69. The reason for this is that the length of the threaded portion is selected so that it will completely discharge the contents of the carpule but go no farther. With some prior art devices which do not have this limiting scheme, it was possible to keep pressing on the actuating lever after the contents had been completely discharged from the device, breaking the carpule and making it difficult to remove the pieces and clean.

FIG. 5 shows a refinement of the invention wherein a relatively stiff metal tube, curved at an appropriate angle, and designated 71 is attached to a threaded holder 73 which has internal threads adapted to mate with a third set of threads 75 on nosepiece 21. It is frequently necessary to inject a medication at an angle through the device and ordinarily needles such as 33 are flexible enough so that they can be turned. However, they have very little strength so that one cannot exert any substantial pressure on inserting the needle at an angle. Utilizing the stiff tube 71, the cannula will extend through the tube with the help of the tunnel-like portion 72, following the angle of the tube, and be reinforced so that a substantial amount of force can be placed on the cannula even when it is at a right angle to the tubular member.

The tubular portion 22 of nosepiece 21 is of sufficient length so that when the device is disassembled, the exhausted carpule will be retained by the nosepiece from which it is easily removed. However, should it stick in cylinder 15, one can easily ram it out.

Many departures can be made from the exact structure shown without departing from the spirit of this invention.

Subject matter to be claimed is:

1. A high pressure dental syringe comprising in combination:
   a. an elongated cylindrical chamber without a holding handle for receiving a carpule containing a medication, said elongated cylindrical chamber having two separable main body parts, each body part being of at least carpule length and having connecting means at one end thereof for positively securing the two parts together at the mid-area of said elongated cylindrical chamber after said carpule has been inserted completely into one of said two parts;
   b. actuating means arranged so that the elongated cylindrical chamber can be held in the palm of a user's hand and be operated by the user's thumb and/or fingers including an operating handle pivotably mounted on the other of said two parts of said cylinder, the free end of said operating handle directed towards the area of said connecting means for said two parts of said cylindrical chamber and being biased outwardly to a first position at an acute angle to said chamber and being movable to a second position parallel to said chamber;
   c. an elongated one-piece piston rod without any projections thereon movable within said chamber for directly engaging one end of said carpule, said one-piece rod having a plurality of ratchet teeth thereon;
   d. A ratchet pivoted to said operating handle and extending into said chamber in operative relationship to engage said ratchet teeth and to force said piston rod toward the distal end of said cylindrical chamber;
   e. means biased into said ratchet teeth to permit said piston rod to move in said cylindrical chamber for exerting force on said carpule but to prevent reverse motion of said piston rod and thus release of the force on said carpule;
   f. a cannula extending from the distal end of said cylindrical chamber whereby:
   g. movement of said operating handle will force said piston rod against the carpule to discharge liquid from said carpule out through said cannula at high pressure.

2. The syringe of claim 1 having a nosepiece at the distal end, said nosepiece being adapted to hold a double cannula with one end extending into the chamber and the other end extending outwardly.

3. The syringe of claim 2 wherein said nosepiece is adapted to retain said carpule within said chamber.

4. The syringe of claim 1 wherein the connecting means for positively securing the two main body parts of said elongated chamber together includes a male portion having connecting structure externally thereof and a female portion having mating connecting structure associated therewith.

5. The syringe of claim 1 wherein the proximal end of said piston rod is smooth and the distal end only has ratchet teeth whereby the movement of said piston rod is limited to prevent it from being forced to the distal end of said chamber.

6. In an anesthetic syringe in accordance with claim 1, a stiff tube extending around said cannula and terminating short of the end, said tube being bent at an angle to said cannula whereby said tube bends and reinforces said cannula.

7. A high pressure dental syringe comprising in combination:
   a. a two-part main body cylindrical chamber for receiving a carpule containing a medication, each of said body parts being of at least carpule length;
   aa. connecting means for detachably securing said two main body parts together;
   b. an operating handle pivoted to one part of said cylindrical chamber and extending from the pivot point toward the distal end of said syringe, said operating handle being biased outwardly to a first position at an acute angle to said chamber and being movable to a second position parallel to said chamber;
   c. an elongated one-piece piston rod without any projections movable within said chamber, said rod having a plurality of ratchet teeth thereon;
   d. a pawl pivoted to said operating handle and extending into said chamber in operative relationship to said ratchet teeth for engaging same to force said piston rod toward the distal end of said cylindrical chamber, yet still permitting said one-piece piston rod to be pulled through said one part of the chamber;
   e. another pawl biased into said ratchet teeth to permit said piston rod to move into and completely through the one part of the chamber but which will function to prevent reverse motion thereof in the chamber;
   f. a cannula extending from the distal end of said cylindrical chamber whereby:
   g. movement of said operating handle will force said piston rod into the other part of said chamber to discharge liquid from said carpule out through said cannula at high pressure.

8. In a high pressure dental syringe in accordance with claim 7, an attachment means for bending and reinforcing said cannula having a stiff tube extending around said cannula and terminating short of the end, said stiff tube being bent at an acute angle up to a right angle to said cylindrical chamber whereby said tube bends and reinforces said cannula.

9. The syringe of claim 8 wherein said connecting means for detachably securing said two parts of said cylindrical chamber includes a male portion having threads externally thereof and a female portion having threads internally thereof.

10. The dental syringe of claim 9 having a nosepiece at the distal end of said cylindrical chamber, said nosepiece being adapted to hold a double cannula with one end extending into the chamber and the other end extending outwardly, said nosepiece being further adapted to retain a carpule within said cylindrical chamber.

11. The syringe of claim 7 wherein said connecting means for detachably securing said two parts of said cylindrical chamber includes a male portion having threads externally thereof and a female portion having threads internally thereof.

12. The dental syringe of claim 7 having a nosepiece at the distal end of said cylindrical chamber, said nosepiece being adapted to hold a double cannula with one end extending into the chamber and the other end extending outwardly, said nosepiece being further adapted to retain a carpule within said cylindrical chamber.

13. A dental syringe for use in administrating an interaligamentary anesthesia comprising:
- an elongated tubular portion;
- an elongated single piece piston rod without any extensions therefrom within said elongated tubular portion;
- said elongated tubular portion having a first tubular cylinder of at least an anesthesia carpule length and a second tubular cylinder also of at least such length;
- means for removably but securely attaching said first and second tubular cylinders together to form said elongated tubular portion;
- the first tubular cylinder having actuating means therewith for effecting movement of said elongated single piece piston rod therethrough;
- said actuating means including an operating lever pivotably mounted externally of said first tubular cylinder, said operating lever having a free end pointed toward the second tubular cylinder;
- further means pivotably connected to said operating lever so that when the free end thereof is actuated a positive movement of said elongated piston rod is effected without the use of any springs on the piston rod; and
- said second tubular cylinder having means therewith for holding a carpule having anesthesia therewithin and for receiving a double cannula affixed thereto.

14. A syringe as set forth in claim 13, wherein said further means comprises a ratchet pivoted to said operating lever and extending into engagement with said elongated piston rod through a slot provided in said first tubular cylinder;
- bias means between said operating lever and said ratchet for effecting outward bias of said lever to a position at an acute angle to said first tubular cylinder;
- said operating lever having its free end movable from the biased outward position to a position substantially parallel to said first tubular cylinder and thereby effecting movement of said ratchet;
- said elongated single piece piston rod without extensions being provided with ratchet teeth thereon for engagement by said ratchet so that said piston rod will be forced into said second tubular cylinder and against said carpule for discharging anesthesia that is contained therewithin.

15. A syringe as set forth in claim 14, wherein said ratchet teeth on said elongated single piece piston rod only extend over the forward portion thereof and the rear portion of said single piece piston rod is smooth so that said ratchet can only effect movement of said piston rod a given distance into said second tubular cylinder to prevent damage to said carpule containing anesthesia mounted within said second tubular cylinder.

16. A syringe as set forth in claim 15, further including detent means for preventing reverse movement of said elongated single piston rod with respect to said first tubular cylinder.

17. A syringe as set forth in claim 16, further including attachment means mountable on the cannula end of said second tubular cylinder for bending and reinforcing a cannula affixed thereto at an acute angle to the longitudinal axis of said tubular portion.

18. A syringe as set forth in claim 14, wherein said bias means between said operating lever and said ratchet includes a spring between the ratchet pivoted to the operating handle.

19. A syringe as set forth in claim 14, wherein said means for removably but securely attaching said first and second tubular cylinders together includes a male threaded portion on one of said tubular cylinders and a complementary female threaded portion on the other tubular cylinder.

20. A syringe as set forth in claim 14, wherein said means with said second tubular cylinder for holding a carpule with anesthesia therein includes a removable portion attached to the distal end of said second tubular cylinder.

* * * * *